US00PP35213P2

(12) United States Plant Patent
Quinn

(10) Patent No.: US PP35,213 P2
(45) Date of Patent: Jun. 6, 2023

(54) ***PANICUM* PLANT NAMED 'RED FLAME'**

(50) Latin Name: *Panicum virgatum*
Varietal Denomination: Red Flame

(71) Applicant: Martin Quinn, Goderich (CA)

(72) Inventor: Martin Quinn, Goderich (CA)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,745

(22) Filed: Nov. 4, 2022

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt

(57) ABSTRACT

The new and distinct cultivar of ornamental grass named *Panicum virgatum* 'Red Flame' with blue-green foliage that develops bright wine coloration in late summer on a large portion of the upper foliage, with upright and arching habit and dense culms producing airy panicles of burgundy, suitable as a multi-seasonal interest as a mass or specimen landscaping, potted plant, and for cut flower arrangements.

1 Drawing Sheet

Botanical classification: *Panicum virgatum.*
Variety denomination: 'Red Flame'.

STATEMENT REGARDING PRIOR DISCLOSURES UNDER 37 CFR 1.77(B)(6)

The first non-enabling information of the claimed plant was the photograph and brief description on a website operated by Walters Gardens, Inc. on Feb. 1, 2022. The claimed plant was first sold on May 16, 2022, by Walters Gardens, Inc. to Blue Sky Nursery who obtained the plant and all information relating thereto, from the inventor. No plants of *Panicum* 'Red Flame' have been sold in this country or anywhere in the world, nor has any disclosure of the new plant been made more than one year prior to the filing date of this application, and such sale or disclosure within one year was either derived directly or indirectly from the inventor.

BACKGROUND OF THE PLANT

*Panicum virgatum* 'Red Flame', hereinafter also referred by the cultivar name 'Red Flame' and the "new plant" is a new and distinct cultivar of Switchgrass. The cross was performed in the summer of 2017 by the inventor with 'Huron Solstice' U.S. Plant Pat. No. 21,498 as the female or seed parent and 'Rostrahlbush' (not patented) in the inventor's garden at Goderich, Ontario, Canada. The seed was collected by the inventors in the autumn of 2017. The single seedling was initially selected from among many for further observation in the summer of 2018 and for final field evaluation in the fall of 2020 at a nursery in Bayfield, Ontario, Canada.

The new plant has been successfully propagated by division at the same nursery in Bayfield, Ontario and later by tissue culture and found to produce identical plants that maintain the unique characteristics of the original plant in multiple generations. The plant is stable and reproduces true to type in successive generations of asexual reproduction.

BRIEF SUMMARY OF THE PLANT

*Panicum virgatum* 'Red Flame' differs from its female parent in that 'Huron Solstice' is taller and has more upright foliage. The male parent is more upright in habit, and the fall color is more reddish purple and less bright wine-colored.

The nearest comparison varieties known to the inventors are: 'Apache Rose' U.S. Plant Pat. No. 29,142, 'Cheyenne Sky' U.S. Plant Pat. No. 23,209, 'RR1' U.S. Plant Pat. No. 17,944, 'Shenandoah' (not patented), and 'Prairie Fire' U.S. Plant Pat. No. 19,367.

'Apache Rose' is much taller in habit and slightly more upright and the leaves are more blue and less flushed with burgundy. 'Cheyenne Sky' has a smaller, deeper burgundy and less bright wine coloration in the late summer color with less saturation of reddish color. 'Shenandoah' is taller and more upright in habit, less vigorous, with less reddish saturation that develops later in the fall. 'RR1' U.S. Plant Pat. No. 17,944 (more commonly known as 'Ruby Ribbons') is significantly shorter in habit. 'Prairie Fire' has a slightly taller habit, and the fall foliage color is more greyed-purple and not as bright wine-colored. 'Red Flame' begins the bright wine coloration in late July and is more vigorous than all of the above-listed comparison cultivars.

The following traits of *Panicum virgatum* 'Red Flame', in combination, have been repeatedly observed in multiple generations of asexually propagated plants and distinguish the new plant from all other switch grass plants known to the inventor:

1. Bluish-green foliage that develops significant bright wine color in late summer on a large portion of the upper foliage;
2. Upright and arching habit with dense culms;
3. Airy panicles of burgundy;
4. Strong vigorous growth habit.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
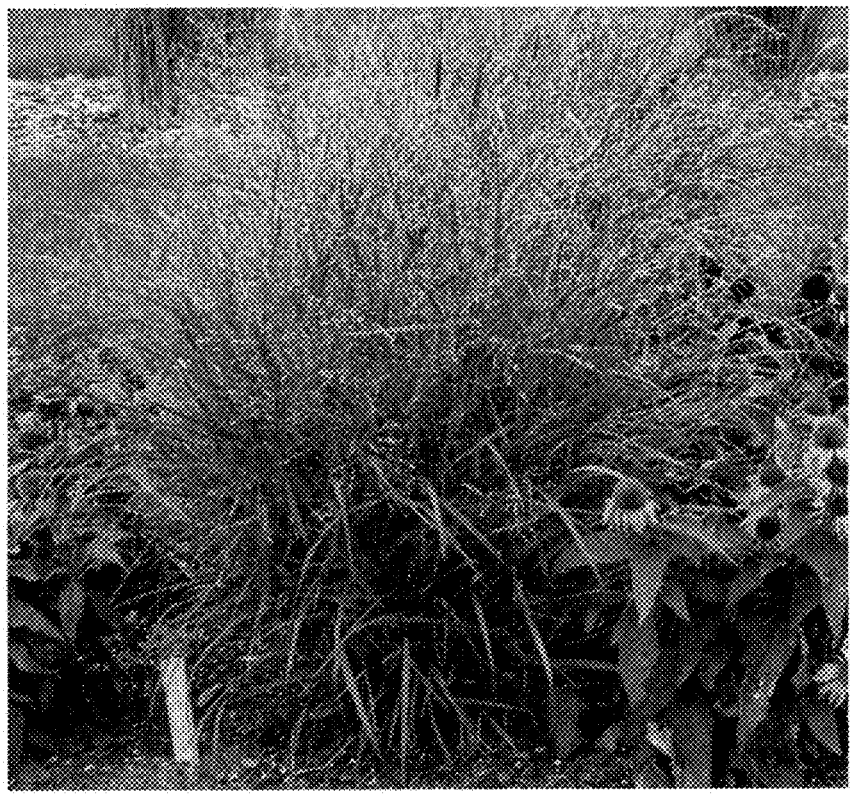
FIG. 1 shows a two-year-old plant in a trial garden in Zeeland, Mich. inflorescence in early to mid-October.
Figure 2:
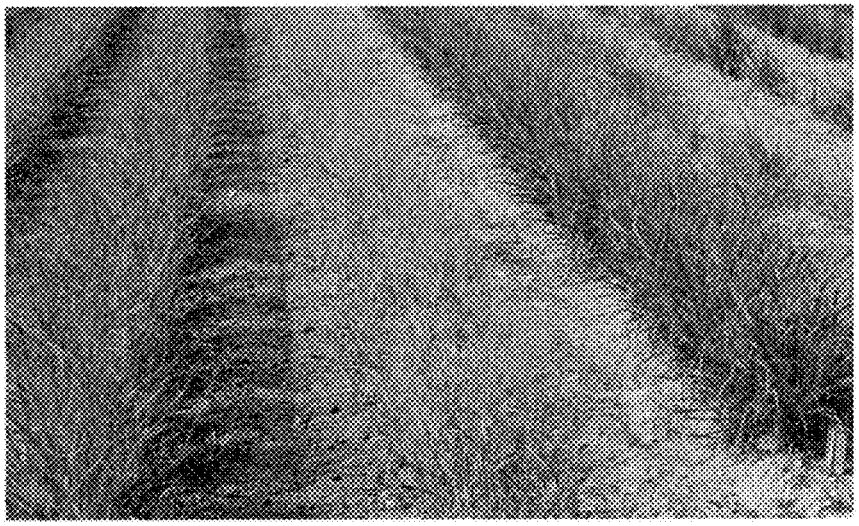
FIG. 2 shows a cultivar comparison of one-year-old plants in a trial field in Bayfield, Ontario, Canada, prior to flowering, with 'Shenandoah' in the left row, 'Rostrahlbush' in the center, and 'Red Flame'.

The following descriptions and color references are based on the 2015 edition of The Royal Horticultural Society Colour Chart except where common dictionary terms are used. The new plant, 'Apache Rose', has not been observed in all possible environments. The phenotype may vary slightly with different environmental conditions, such as temperature, light, fertility, moisture, and maturity levels, but without any change in the genotype. The following observations and size descriptions are of a four-year-old plant in a trial garden of a wholesale perennial nursery in Zeeland, Mich., USA in full sun with supplemental water and fertilizer as needed.

Parentage: Female (seed parent) *Panicum virgatum* 'Huron Solstice' x male (pollen patent) 'Rotstrahlbush';

Propagation:

Method: By division of the culms and sterile shoot-tip tissue culture;

*Time to finishing in a* 3.8-*liter pot*.—About 10 weeks.

*Rooting habit*.—Normal, coarsely branching; root color nearest RHS 155D.

*Vigor*.—Rapid.

Plant description:

Plant shape and habit: Hardy herbaceous perennial forming tightly rhizomatous clump, with upright culms and arching foliage, topped with finely textured airy panicles that are wider than tall in maturity;

Plant size: Foliage height at flowering is about 100 cm tall from soil line to the top of the foliage and 120 cm tall to top of flowers; about 35 cm wide at soil line and about 150 cm at widest point about 90 cm above soil;

Foliage description: Glabrous, with microscopic marginal dentations, flat, alternate along culm, arching, sheathed from node of attachment to ligule, linear; adaxial and abaxial surfaces dull; deciduous but persist through winter;

Foliage size: To about 51 cm long and about 10 mm wide, shorter distally, with sheath portion to about 15 cm long, totally to 66 cm long; averaging about 50 cm and 9 mm wide;

Foliage color: Adaxial surface early season and young foliage nearest RHS 138A; Abaxial surface early season and young foliage between RHS 146B and RHS 146A; Adaxial surface midseason between RHS N186C and RHS 187B in the distal one-half to five-sixths and the proximal portion between RHS N138B and RHS 147B; Abaxial surface midseason: between RHS 187C and RHS 187B in the distal one-half to three-quarters, and proximally nearer the culm between RHS N138B and RHS 147B; Adaxial late season in the distal one-half to five-sixths between RHS N186A and RHS 187A, proximally between RHS N138B and RHS 147B; Abaxial late season in distal one-half to three-quarters between RHS N186A and RHS 187A, proximally between RHS N138B and RHS 147B;

Veins: Parallel; midrib about 0.7 mm across; adaxial recessed, abaxial costate and smooth; adaxial midrib color between RHS N138B and RHS 147B distally becoming between RHS N186A and RHS 187A, abaxial midrib nearest RHS 138A proximally and nearest RHS 187A distally, color of secondary veins same as the surrounding leaf on both the top and bottom of the leaf;

Culm (stem): Erect; terete; glabrous; glaucous proximally; dull surface; 75% enclosed by leaf sheath; about 5 nodes per culm; about 160 per clump;

Culm dimension: To about 56 cm long without panicle, average about 51 cm; including panicle to about 84 cm long, with average about 81.0 cm; about 3.5 mm diameter at base; internode length average about 73 cm;

Culm color: Nearest RHS N146D proximally, distally nearest RHS 137B; Node description: about 5 per culm, slightly swollen to about 4 mm diameter; color nearest RHS 197B;

Inflorescence: Finely branched open panicle, one panicle per culm;

Flower timing: Beginning early August, flowering through late August and panicles dry and remain effective through winter;

No fragrance detected;

Panicle: Pyramidal; to about 41 cm tall and 32 cm wide; overall effective color RHS 187A;

Rachis: Terete, branched, glabrous, glaucous; about 58 cm long and about 2 mm at base; branches to about 27 cm long and about 0.7 mm diameter held at about 45 to 60 degrees angle above horizontal; color nearest RHS 137B;

Pedicel: Thin; terete; between 2 mm and 12 mm long and about 0.2 mm diameter; color nearest RHS 137A with moderate blush on dorsal portion of nearest RHS 187A;

Rachilla: Thin; about 2 min long and 0.2 mm diameter; color nearest RHS 137B;

First glume: About 4 mm long and 1 mm wide; with truncate clasping base and acute apex; color between RHS 187B and RHS 187A;

Second glume: About 4 mm long and 2 mm wide; with truncate clasping base and acute apex; color between RHS 187B and RHS 187A;

Lemma:

*Outer and inner*.—Both about 3 mm long and 1.5 mm wide; with truncate clasping base and acute apex; color between RHS 187B and RHS 187C on surfaces exposed to sun and between RHS 138B and RHS 145B in areas minimally exposed to sun.

Spikelet: Usually with 2 flowers, 1.5 to 2.5 cm long and 2.5 mm wide; flowering on rachis;

Gynoecium:

*Stigma*.—Two, feathered, protruding about 1.5 mm from glume; color nearest RHS 187A.

Androecium:

*Filaments*.—Fine, hair-like, white, less than 0.1 mm diameter and up to 2.0 mm long.

Anthers: Two or three; dorsifixed, longitudinal; about 2.5 mm long and about 1.0 mm wide; color nearest RHS N25A;

Pollen: Round, less than 0.1mm in diameter; nearly transparent; abundant; color lighter than RHS 155D;

Fruit: Caryopsis; about 2.5 mm long and about 1.5 mm wide; color nearest RHS 164C;

Growth and hardiness: The plant is very drought once established. Hardiness at least from USDA zone 4 through 9.

Pest and disease resistance: Rust diseases such as *Puccinia* ssp. have not been observed. Other disease and pest resistance beyond what is typical of that of other Switch Grasses has not been observed.

I claim:

1. A new and distinct cultivar of switchgrass *Panicum virgatum* plant named 'Red Flame' as herein described and illustrated.

* * * * *